United States Patent
Shi et al.

(10) Patent No.: US 10,155,061 B2
(45) Date of Patent: Dec. 18, 2018

(54) ENZYMATIC WOUND DEBRIDING COMPOSITIONS WITH ENHANCED ENZYMATIC ACTIVITY

(71) Applicant: SMITH & NEPHEW, INC., Memphis, TN (US)

(72) Inventors: Lei Shi, Mansfield, TX (US); Aleksa Jovanovic, Fort Worth, TX (US); Duncan Aust, Huntingdon Valley, PA (US)

(73) Assignee: Smith & Nephew, Inc., Memphis, TN (US)

(*) Notice: Subject to any disclaimer, the term of this patent is extended or adjusted under 35 U.S.C. 154(b) by 110 days.

(21) Appl. No.: 15/358,937

(22) Filed: Nov. 22, 2016

(65) Prior Publication Data

US 2017/0072029 A1    Mar. 16, 2017

Related U.S. Application Data

(62) Division of application No. 13/514,945, filed as application No. PCT/US2010/059409 on Dec. 8, 2010, now Pat. No. 9,694,100.

(Continued)

(51) Int. Cl.
*A61K 38/48* (2006.01)
*A61L 15/26* (2006.01)
(Continued)

(52) U.S. Cl.
CPC .............. *A61L 15/26* (2013.01); *A61K 9/06* (2013.01); *A61K 9/10* (2013.01); *A61K 38/488* (2013.01); *A61K 38/4826* (2013.01); *A61K 38/4873* (2013.01); *A61K 38/4886* (2013.01); *A61K 47/10* (2013.01); *A61K 47/44* (2013.01); *A61L 15/34* (2013.01); *A61L 15/38* (2013.01);
(Continued)

(58) Field of Classification Search
None
See application file for complete search history.

(56) References Cited

U.S. PATENT DOCUMENTS

| | | | |
|---|---|---|---|
| 3,705,083 A | 12/1972 | Chiulli et al. | 435/220 |
| 3,821,364 A | 6/1974 | Chiulli | 424/94.67 |

(Continued)

FOREIGN PATENT DOCUMENTS

| | | |
|---|---|---|
| JP | T 2005-528425 | 9/2005 |
| JP | 2007505107 | 3/2007 |

(Continued)

OTHER PUBLICATIONS

"Xenaderm Ointment." Xenaderm Ointment. Healthpoint, Ltd., Jun. 2010. Web. Aug. 14, 2012. <http://dailymed.nlm.nih.gov/dailymed/archives/fdaDrugInfo.cfm?archiveid=25386>.

(Continued)

*Primary Examiner* — Erin M. Bowers
(74) *Attorney, Agent, or Firm* — Norton Rose Fulbright US LLP

(57) ABSTRACT

The present invention is directed to topical enzymatic wound debriding compositions with enhanced enzymatic activity. These compositions comprise a dispersed phase comprising at least one proteolytic enzyme and at least one hydrophilic polyol; and a continuous phase comprising a hydrophobic base.

14 Claims, 10 Drawing Sheets

Activity of Thermolysin in Eschar Model as a Function of PEG-400 Concentration in White Petrolatum

Related U.S. Application Data

(60) Provisional application No. 61/267,730, filed on Dec. 8, 2009.

(51) Int. Cl.
| | | |
|---|---|---|
| *A61L 15/34* | (2006.01) | |
| *A61L 15/38* | (2006.01) | |
| *A61L 15/44* | (2006.01) | |
| *A61L 26/00* | (2006.01) | |
| *A61K 9/06* | (2006.01) | |
| *A61K 9/10* | (2006.01) | |
| *A61K 47/10* | (2017.01) | |
| *A61K 47/44* | (2017.01) | |

(52) U.S. Cl.
CPC .......... *A61L 15/44* (2013.01); *A61L 26/0019* (2013.01); *A61L 26/0066* (2013.01); *C12Y 304/24027* (2013.01); *A61L 2300/254* (2013.01)

(56) References Cited

U.S. PATENT DOCUMENTS

| | | | |
|---|---|---|---|
| 3,892,856 A | 7/1975 | Hill et al. | 514/174 |
| 4,017,615 A | 4/1977 | Shastri et al. | 514/174 |
| 4,070,462 A | 1/1978 | Ecker | 514/179 |
| 5,332,503 A | 7/1994 | Lee et al. | 210/635 |
| 5,422,103 A | 6/1995 | Stern et al. | 424/78.06 |
| 5,422,261 A | 6/1995 | Lee et al. | 435/219 |
| 5,439,935 A * | 8/1995 | Rawlings | A61K 8/66 514/451 |
| 5,514,370 A | 5/1996 | Stern et al. | 424/78.06 |
| 5,560,910 A | 10/1996 | Crandall | 424/94.63 |
| 5,578,310 A | 11/1996 | M'Timkulu et al. | 424/401 |
| 5,718,897 A | 2/1998 | Herman | 424/94.67 |
| 5,827,531 A | 10/1998 | Morrison et al. | 424/450 |
| 5,851,522 A | 12/1998 | Herman | 424/94.67 |
| 5,908,707 A | 6/1999 | Cabell et al. | 428/537.5 |
| 6,074,664 A | 6/2000 | Roreger et al. | 424/443 |
| 6,146,626 A | 11/2000 | Markert et al. | 424/94.63 |
| 6,238,683 B1 | 5/2001 | Burnett et al. | 424/405 |
| 6,361,783 B2 | 3/2002 | Moaddel et al. | 424/401 |
| 6,399,092 B1 | 6/2002 | Hobson et al. | 424/443 |
| 6,479,060 B1 | 11/2002 | Jones et al. | 424/401 |
| 6,489,358 B2 | 12/2002 | Lavon et al. | 514/460 |
| 6,548,556 B2 | 4/2003 | Hobson et al. | 514/772.4 |
| 6,958,150 B2 | 10/2005 | Wegman et al. | 424/94.67 |
| 7,101,563 B1 | 9/2006 | Vromen | 424/401 |
| 7,166,281 B2 | 1/2007 | Kennedy | 424/94.65 |
| 7,241,456 B2 | 7/2007 | Vromen | 424/449 |
| 7,429,377 B2 | 9/2008 | Artamonov et al. | 424/94.2 |
| 2003/0072750 A1 | 4/2003 | Rosenberg | |
| 2003/0091540 A1 | 5/2003 | Ahmad et al. | 424/93.3 |
| 2003/0170225 A1 | 9/2003 | Soroff et al. | 424/94.63 |
| 2003/0198631 A1 | 10/2003 | Shi | 424/94.63 |
| 2003/0198632 A1 | 10/2003 | Shi | 424/94.63 |
| 2004/0091539 A1 | 5/2004 | Lindahl et al. | 424/484 |
| 2005/0036950 A1 | 2/2005 | Jones et al. | 424/45 |
| 2005/0113731 A1 | 5/2005 | Qvist | 602/48 |
| 2005/0281806 A1 | 5/2005 | Trumbore et al. | 424/94.65 |
| 2006/0115500 A1 | 6/2006 | Aukunuru et al. | 424/400 |
| 2006/0127437 A1 | 6/2006 | Kennedy et al. | 424/422 |
| 2006/0222639 A1 | 10/2006 | Soroff et al. | 424/94.64 |
| 2007/0003541 A1 | 1/2007 | Faudoa et al. | 424/94.65 |
| 2007/0004037 A1 | 1/2007 | Faudoa | 435/325 |
| 2007/0166251 A1 | 7/2007 | Dayan et al. | 424/62 |
| 2008/0014169 A1 | 1/2008 | Trumbore et al. | 424/78.08 |
| 2008/0206228 A1 | 8/2008 | Vaccaro et al. | 424/94.67 |

FOREIGN PATENT DOCUMENTS

| | | |
|---|---|---|
| JP | T 2007-505107 | 3/2007 |
| WO | WO 1996/023487 | 8/1996 |
| WO | WO 2002/051436 | 7/2002 |
| WO | WO 2003/088993 | 10/2003 |
| WO | WO 2004/064882 | 8/2004 |
| WO | WO2005/025548 | 3/2005 |
| WO | WO 2006/037606 | 4/2006 |
| WO | WO 2006/135506 | 12/2006 |
| WO | WO 2007/050543 | 5/2007 |

OTHER PUBLICATIONS

"Santyl® Ointment". Collagenase Santyle Ointment. Healthpoint, Ltd., 2009.
Byrne, K.: "Factors affecting Enzyme Activity", Bio Factsheet, Apr. 1999, No. 43, pp. 1-3.
Fao, http://www.fao.org/ag/agn/jecfa-additives/specs/Monograph1/Additive-316.pdf (accessed Oct. 28, 2014).
Office Communication issued in Japanese Patent Application No. 2012-543231, dated Jan. 22, 2014.
PCT International Search Report and Written Opinion issued in PCT Patent Application No. PCT/US2010/059409, dated May 3, 2011.
PCT IPRP issued in PCT Patent Application No. PCT/US2010/059409, dated Mar. 14, 2012.
Rowe, R. C. et al.: "Glycerin", Handbook of Pharmaceutical Excipients, fifth edition, 2006, p. 301-303.
Rowe, R.C. et al.: "Polyethylene glycol", Handbook of Pharmaceutical Excipients, fifth edition, 2006, p. 545-550.
Shi et al, "Study on the debridement efficacy of formulated enzymatic wound debriding agents by in vitro assessment using artificial wound eschar and by an in vivo pig model", *Wound Repair Regen*, 17(6):853-862, 2009.

* cited by examiner

Activity of Collagenase in Eschar Model as a Function of PEG-400 Concentration in White Petrolatum Activity of Collagenase in Eschar Model as a Function of PEG-600 Concentration in White Petrolatum Activity of Collagenase in Eschar Model as a Function of Poloxamer 124 (POL-124)
Concentration in White Petrolatum Activity of Trypsin in Eschar Model as a Function of PEG-400 Concentration in White Petrolatum Activity of Papain in Eschar Model as a Function of PEG-400 Concentration in White Petrolatum Activity of Thermolysin in Eschar Model as a Function of PEG-400 Concentration in White Petrolatum Activity of Pepsin in Eschar Model as a Function of PEG-400 Concentration in White Petrolatum Collagenase Release as a Function of PEG-400 Concentration in White Petrolatum Enzyme Stability (Stored at Room Temperature) in PEG-in-White Petrolatum Dispersion vs. Oil-in-Water Emulsion Cream Debridement Efficacy in Eschar Removal in Pig Burn Wounds

ENZYMATIC WOUND DEBRIDING COMPOSITIONS WITH ENHANCED ENZYMATIC ACTIVITY

CROSS-REFERENCE TO RELATED APPLICATIONS

This application is a divisional application of U.S. application Ser. No. 13/514,945, filed 8 Jun. 2012, which is a national phase application under 35 U.S.C. § 371 of International Patent Application No. PCT/US2010/059409, filed 8 Dec. 2010, which claims the benefit of U.S. Provisional Application No. 61/267,730, filed 8 Dec. 2009. The contents of the referenced applications are incorporated into the present application by reference.

BACKGROUND OF THE INVENTION

A. Field of the Invention

The present invention relates generally to topical enzymatic wound debriding compositions and methods of treating wounds in need of debridement.

B. Background

The healing of wounds is a complex process which is often further complicated by the presence of non-viable, necrotic tissue in the wound area. Debridement is the process of removing the non-viable tissue from a wound to prevent or diminish infection and facilitate healing. Topical compositions containing proteolytic enzymes such as trypsin, papain, bromelain, subtilisin, sutilains, and collagenase have been used for enzymatic wound debridement. Generally, the standard of care is to apply the composition to the wound in need of debridement once daily (once every 24 hours) or more often if the composition becomes soiled. Because many proteolytic enzymes are susceptible to degradation in water-based compositions, many wound debriding compositions are made with anhydrous, hydrophobic bases such as petrolatum, mineral oil and/or vegetable oil as disclosed in U.S. Pat. No. 3,821,364 and U.S. Pat. No. 6,479,060, both of which are herein incorporated by reference. However, enzymatic wound debriding compositions based on hydrophobic bases are generally not miscible in the aqueous environment of a wound bed, and thus contact of the proteolytic enzyme with the wound bed is generally hindered. Some other compositions are made with anhydrous, hydrophilic bases such as propylene glycol or poloxamers as disclosed in U.S. Pat. No. 6,548,556, US 2003/0198631 and US 2003/0198632, all of which are herein incorporated by reference.

SUMMARY OF THE INVENTION

The present invention is directed to topical enzymatic wound debriding compositions with enhanced enzymatic activity. These compositions comprise a dispersed phase comprising at least one proteolytic enzyme and at least one hydrophilic polyol; and a continuous phase comprising a hydrophobic base. The wound debriding compositions of the present invention possess enhanced enzymatic activity over wound debriding compositions of the prior art.

In one aspect of the present invention, there is disclosed a wound debriding composition comprising a dispersed phase comprising a liquid hydrophilic polyol and at least one proteolytic enzyme; and a continuous phase comprising a hydrophobic base; wherein the amount of liquid hydrophilic polyol is within ±10% w/w of the optimum amount of the liquid hydrophilic polyol. For example, if the optimum amount was about 30% w/w, the amount of liquid hydrophilic polyol that could be used would be between about 20% w/w and about 40% w/w of the total formulation to achieve enhanced enzymatic activity of the formulation. In another aspect, the amount of liquid hydrophilic polyol is within ±9%, 8%, 7%, or 6% w/w of the optimum amount of the liquid hydrophilic polyol. In still another aspect, the amount of liquid hydrophilic polyol is within ±5%, 4%, 3%, 2%, 1%, 0.5%, or 0.1% w/w of the optimum amount of the liquid hydrophilic polyol.

The "optimum amount of liquid hydrophilic polyol" in a composition comprising (a) a dispersed phase including a liquid hydrophilic polyol and at least one proteolytic enzyme; and (b) a continuous phase comprising a hydrophobic base can be determined by the method described in Section A of the Detailed Description section of this specification, which is incorporated into this section by reference.

A method for determining whether a composition is within ±10% w/w of the optimum amount of a liquid hydrophilic polyol is described in Section B of the Detailed Description section of this specification, which is incorporated by reference.

The optimum amount of liquid hydrophilic polyol for compositions with different proteolytic enzymes can differ. Additionally, the optimum amount of liquid hydrophilic polyol for compositions with a specific proteolytic enzyme can differ depending on the ingredients of the composition. For example, the optimum amount of liquid hydrophilic polyol in a collagenase composition containing PEG-400 and petrolatum can be different from the optimum amount of liquid hydrophilic polyol in a collagenase composition containing PEG-600 and petrolatum, or different from a collagenase composition containing poloxamer-124 and petrolatum.

The term "hydrophilic polyol" means water-soluble, polar aliphatic alcohols with at least two hydroxyl groups and includes, but is not limited to, polymeric polyols (e.g., polyethylene glycols and poloxamers).

The term "liquid" in the context of describing "hydrophilic polyol", "polyethylene glycol", or "poloxamer" means that the material is in the liquid state at 25° C.

The term "solid" in the context of describing "hydrophilic polyol", "polyethylene glycol", or "poloxamer" means that the material is in the solid state at 25° C.

In another aspect of the present invention, there is disclosed a method of treating a wound in need of debridement comprising: applying to the wound a composition comprising a dispersed phase comprising a liquid hydrophilic polyol, and an effective debriding concentration of at least one proteolytic enzyme; and a continuous phase comprising a hydrophobic base; wherein the amount of liquid hydrophilic polyol is within ±10% w/w of the optimum amount. In another aspect, the amount of liquid hydrophilic polyol is within ±9%, 8%, 7%, or 6% w/w of the optimum amount. In still another aspect, the amount of liquid hydrophilic polyol is within ±5%, 4%, 3%, 2%, 1%, 0.5%, or 0.1% w/w of the optimum amount.

In some embodiments, the proteolytic enzyme is a metalloprotease, a cysteine protease, a serine protease, or an aspartic peptidase. Generally, the optimum amount of hydrophilic polyol for compositions comprising a metalloprotease, a cysteine protease or a serine protease is from about 10%, 11%, 12%, 13%, 14%, 15%, 16% 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% w/w to about 40% w/w, or any range or numerical amount derivable therein. The optimum amount of hydrophilic polyol for compositions comprising an aspartic peptidase is from about 48%, 49%, 50%, 51%, 52%, 53%, 54%, 55%, 56%, 57%, 58%, 59%, 60%, 61%, 62%, 63%, 64%, 65%, 66%, 67% w/w to about 68% w/w or any range or numerical amount derivable therein. In one embodiment the metalloprotease is collagenase. In another embodiment the metalloprotease is collagenase and the optimum amount of the hydrophilic polyol is from about 10%, 11%, 12%, 13%, 14%, 15%, 16% 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% w/w to about 40% w/w or any range or numerical amount derivable therein. In one embodiment, the metalloprotease is thermolysin. In another embodiment, the metalloprotease is thermolysin and the optimum amount hydrophilic polyol is from about 19%, 20%, 21%, 22%, 23%, 24%, 25%, 26%, 27%, 28%, 29%, 30%, 31%, 32%, 33%, 34%, 35%, 36%, 37%, 38% w/w to about 39% w/w or any range or numerical amount derivable therein. In one embodiment, the cysteine protease is papain. In another embodiment the cysteine protease is papain and the optimum amount of the hydrophilic polyol is from about 19%, 20%, 21%, 22%, 23%, 24%, 25%, 26%, 27%, 28%, 29%, 30%, 31%, 32%, 33%, 34%, 35%, 36%, 37%, 38% w/w to about 39% w/w or any range or numerical amount derivable therein. In one embodiment, the serine protease is trypsin. In another embodiment the serine protease is trypsin and the optimum amount of hydrophilic polyol is from about 4%, 5%, 6%, 7%, 8%, 9%, 10%, 11%, 12%, 13%, 14%, 15%, 16% 17%, 18%, 19%, 20%, 21%, 22%, 23% w/w to about 24% w/w or any range or numerical derivable therein. In one embodiment, the aspartic peptidase is pepsin. In another embodiment the aspartic peptidase is pepsin and the optimum amount of hydrophilic polyol is from about 48%, 49%, 50%, 51%, 52%, 53%, 54%, 55%, 56%, 57%, 58%, 59%, 60%, 61%, 62%, 63%, 64%, 65%, 66%, 67% w/w to about 68% w/w or any range or numerical amount derivable therein. In some embodiments, the proteolytic enzyme is suspended in the dispersed phase. In other embodiments the proteolytic enzyme is dissolved in the dispersed phase.

In some embodiments, the liquid hydrophilic polyol is a liquid polyethylene glycol or a liquid poloxamer, or mixtures thereof.

In some embodiments of the present invention, the dispersed phase may further comprise a solid hydrophilic polyol in order to help physically stabilize the composition or reduce or prevent phase separation. In some embodiments, the solid hydrophilic polyol is a solid poloxamer, or a solid polyethylene glycol, or mixtures thereof.

In various embodiments of the present invention, the hydrophobic base comprises petrolatum, mineral oil, or vegetable oil, or mixtures thereof. In one embodiment, the base comprises petrolatum. In another embodiment, the hydrophobic base comprises a vegetable oil. In still another embodiment, the hydrophobic base comprises mineral oil. In a further embodiment, the hydrophobic base comprises petrolatum and mineral oil, petrolatum and vegetable oil, mineral oil and vegetable oil, or petrolatum, mineral oil, and vegetable oil. In still another embodiment, the hydrophobic base comprises a vegetable oil, wherein the vegetable oil is castor oil.

In one embodiment, the composition is a semisolid. In another embodiment, the composition is a liquid. In other embodiments, the composition is impregnated on a pad, gauze, or sponge. In one embodiment, the composition is sterile or anhydrous or both.

The composition can be packaged in any package appropriate for dispensing a wound debrider. The compositions can be packaged in multi-use, single-dose, or metered dose packages. Non-limiting examples include a tube, bottle, jar, pump container, pressurized container, bladder container, aerosol container, aerosol spray container, non-aerosol spray container, syringe, pouch, or sachet.

In another embodiment of the present invention there is disclosed a method of determining the optimum amount of liquid hydrophilic polyol to add to a target composition comprising a dispersed phase including a proteolytic enzyme and a continuous phase including a hydrophobic base, the method comprising: (1) obtaining a series of compositions comprising the dispersed phase and the continuous phase, wherein the dispersed phase further includes a liquid hydrophilic polyol, and wherein each composition in the series of compositions include an identical amount of proteolytic enzyme and a different amount of the liquid hydrophilic polyol; (2) determining the enzymatic activity of each composition in the series of compositions; (3) determining the highest point on a graph that plots the enzymatic activity versus the amount of liquid hydrophilic polyol(s) included in each composition of the series of compositions, wherein the highest point on the graph correlates to the optimum amount of liquid hydrophilic polyol to add to the target composition. In one aspect, the enzymatic activity of the series of compositions can be determined by using the in-vitro artificial eschar testing model as described in this specification.

In a further aspect of the present invention there is disclosed a method of increasing enzymatic activity in a target composition comprising a dispersed phase including a proteolytic enzyme and a continuous phase including a hydrophobic base, the method comprising: (1) obtaining a series of compositions comprising the dispersed phase and the continuous phase, wherein the dispersed phase further includes a liquid hydrophilic polyol, and wherein each composition in the series of compositions includes an identical amount of proteolytic enzyme and a different amount of the liquid hydrophilic polyol; (2) determining the enzymatic activity of each composition in the series of compositions; (3) determining the highest point on a graph that plots the enzymatic activity versus the amount of liquid hydrophilic polyol(s) included in each composition of the series of compositions, wherein the highest point on the graph correlates to an optimum amount of liquid hydrophilic polyol to add to the target composition, and (4) adding ±10% w/w of the optimum amount of liquid hydrophilic polyol to the target composition, thereby increasing the enzymatic activity in the target composition. In one aspect, the enzymatic activity of the series of compositions can be determined by using the in-vitro artificial eschar testing model as described in this specification.

The amount of polyol in the series of compositions can vary from each composition randomly or by a selected amount. In one embodiment, the amount of polyol in each composition of the series of compositions can be 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% by weight or volume of the composition.

The term "anhydrous" means that the compositions contain less than about 5% w/w, or less than about 3% w/w, or less than about 1% w/w, or less than about 0.5% w/w, or less than about 0.1% w/w in relation to the total composition, or 0%, of free or added water, not counting the water of hydration, bound water, or typical moisture levels present in any of the raw ingredients of the compositions.

Unless otherwise specified, the percent values expressed herein are weight by weight and are in relation to the total composition.

The use of the word "a" or "an" when used in conjunction with the term "comprising" or "containing" in the claims and/or the specification may mean "one," but it is also consistent with the meaning of "one or more," "at least one," and "one or more than one."

Throughout this application, the term "about" is used to indicate that a value includes the inherent variation of error for the device obtaining the value, the method being employed to determine the value, or the variation that exists among the objects being evaluated.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The terms "treating," "inhibiting," "preventing, or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The compositions and methods for their use can "comprise," "consist essentially of," or "consist of" any of the ingredients or steps disclosed throughout the specification. With respect to the transitional phase "consisting essentially of," and in one non-limiting aspect, a basic and novel characteristic of the compositions and methods disclosed in this specification includes the composition's enhanced enzymatic activity.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

One aspect of the present invention provides for topical enzymatic wound debriding compositions with enhanced enzymatic activity. These compositions comprise a dispersed phase comprising at least one proteolytic enzyme and a hydrophilic polyol; and a continuous phase comprising a hydrophobic base. In one aspect of the invention, the hydrophilic polyol is a liquid hydrophilic polyol.

It was found that the enzymatic activity (e.g., in vitro collagenolysis) of the compositions of the present invention, which are dispersions of a hydrophilic polyol and a proteolytic enzyme in a hydrophobic base, not only was higher than the enzymatic activity of enzyme compositions based solely on a proteolytic enzyme and hydrophobic base combination (i.e., no hydrophilic phase such as a hydrophilic polyol), but also surprisingly higher than those enzyme compositions based solely on a proteolytic enzyme and hydrophilic base combination (i.e., no hydrophobic phase such as petrolatum). Since enzymes are activated in the presence of moisture, it would have been expected to see the highest enzymatic activity in compositions based solely on a proteolytic enzyme and hydrophilic base combination, where the base would be completely miscible in moisture and conditions would be the most favorable for release and activation of the enzyme. However, the dispersion composition of hydrophilic and hydrophobic phases of the present invention had the highest enzymatic activity correlating to an optimum amount of the hydrophilic polyol which was more than 0% and less than 100% of the hydrophilic polyol in the composition.

Figure 1:
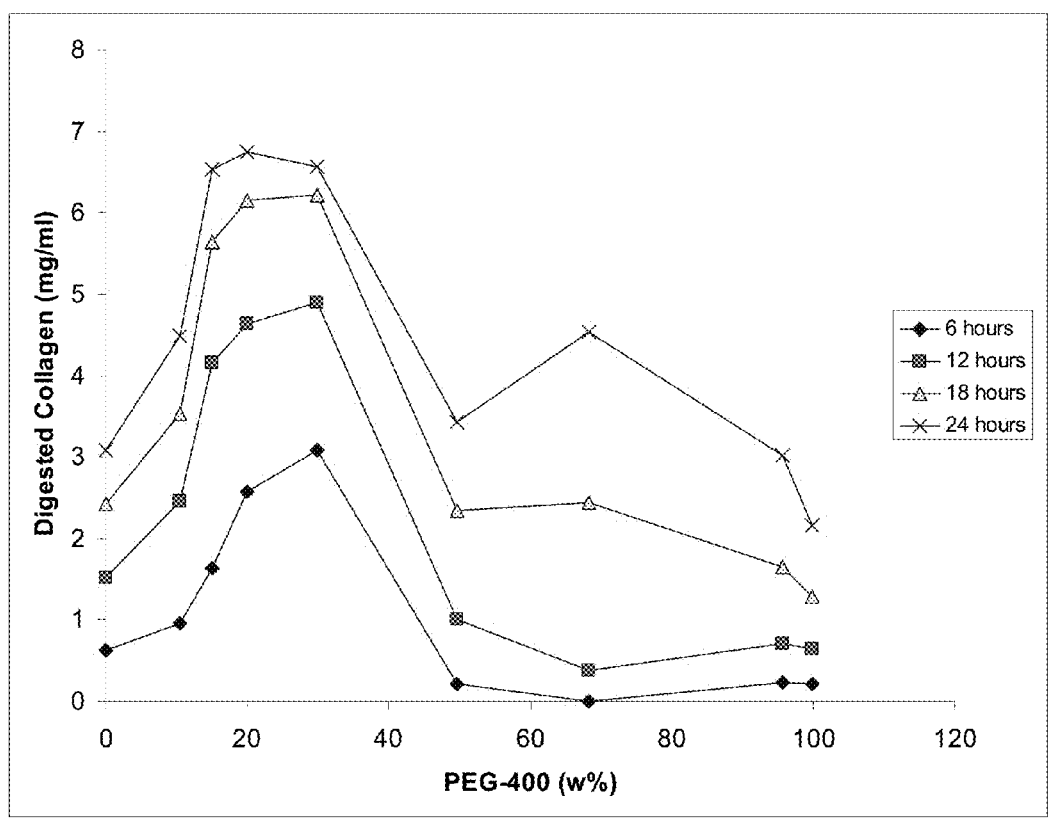
FIG. 1. Plot of the in-vitro collagenolysis activity (mg/ml) of a series of compositions comprising a dispersed phase comprising collagenase and PEG-400, dispersed in a hydrophobic phase comprising white petrolatum (y-axis) versus the percentage of the PEG-400 comprised in the series of compositions (x-axis).
Figure 2:
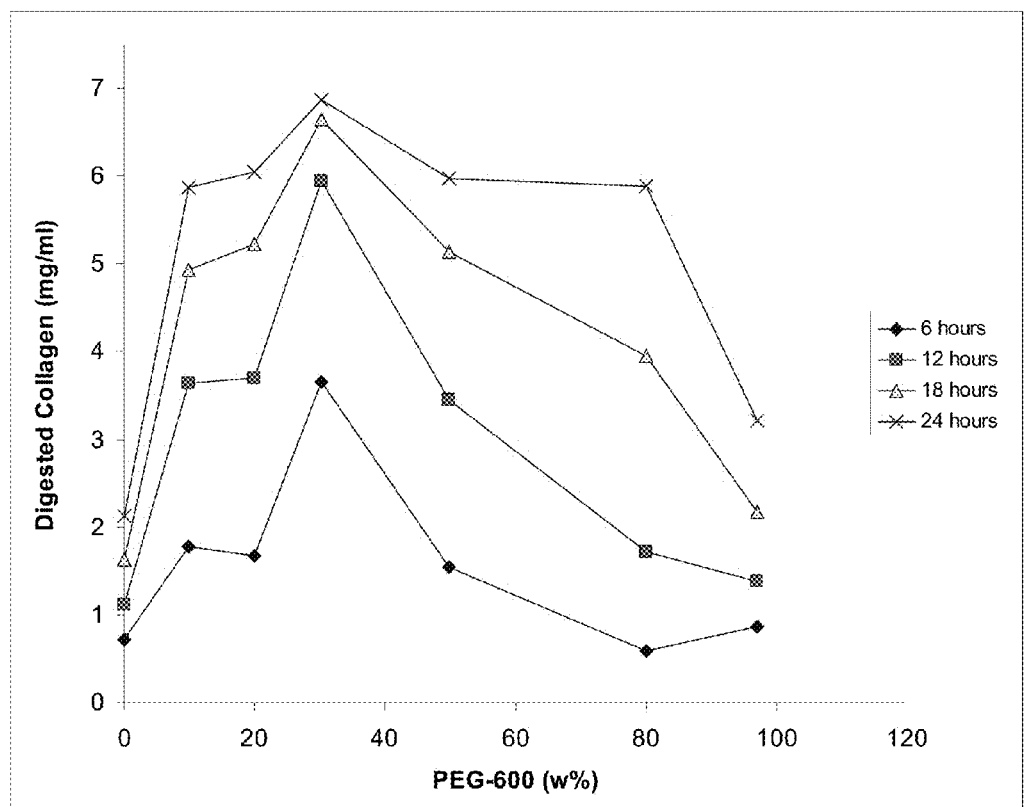
FIG. 2. Plot of the in-vitro collagenolysis activity (mg/ml) of a series of compositions comprising a dispersed phase comprising collagenase and PEG-600, dispersed in a hydrophobic phase comprising white petrolatum (y-axis) versus the percentage of the PEG-600 comprised in the series of compositions (x-axis).
Figure 3:
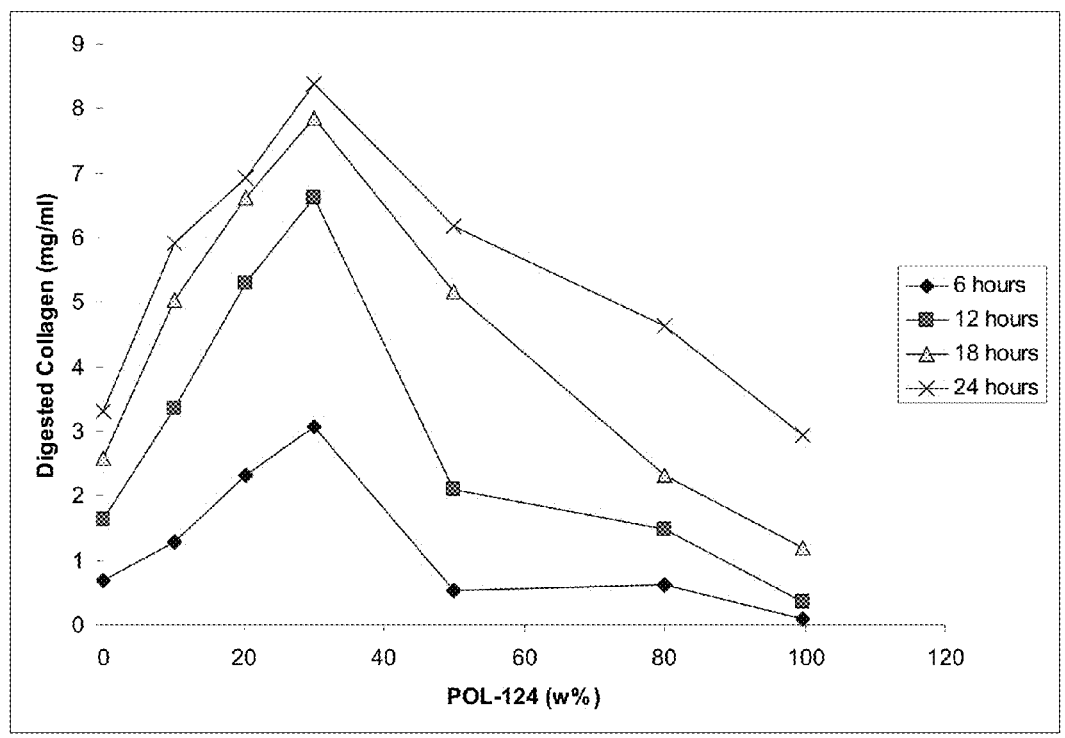
FIG. 3. Plot of the in-vitro collagenolysis activity (mg/ml) of a series of compositions comprising a dispersed phase comprising collagenase and poloxamer-124, dispersed in a hydrophobic phase comprising white petrolatum (y-axis) versus the percentage of the poloxamer-124 comprised in the series of compositions (x-axis).
Figure 4:
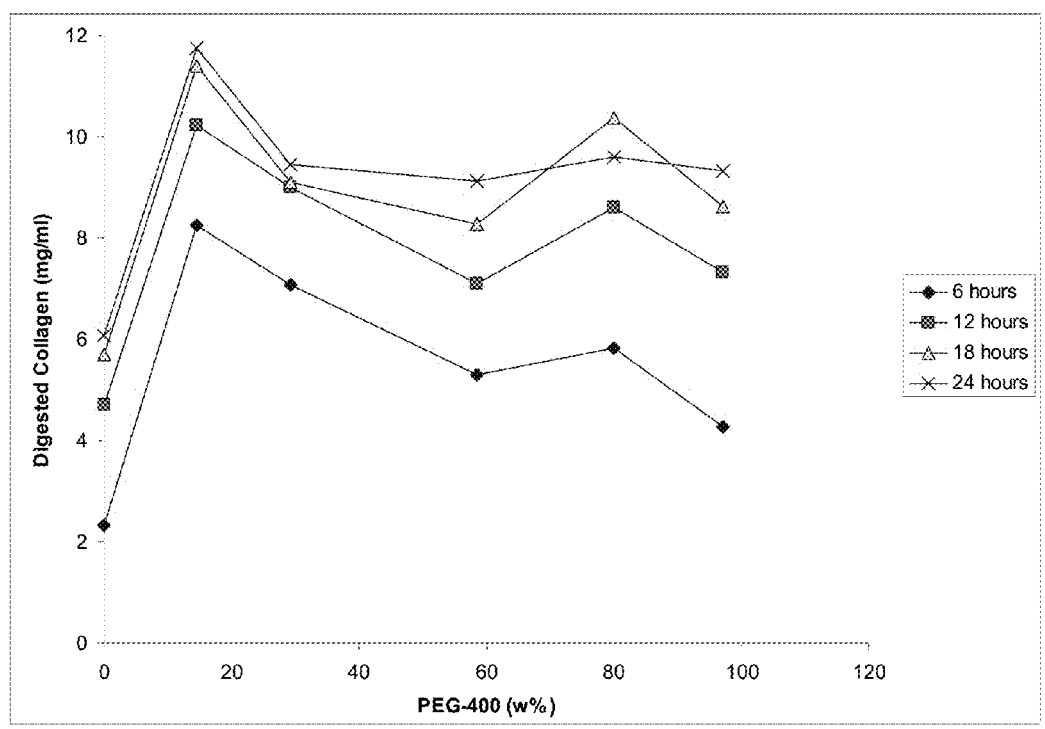
FIG. 4. Plot of the in-vitro collagenolysis activity (mg/ml) of a series of compositions comprising a dispersed phase comprising trypsin and PEG-400, dispersed in a hydrophobic phase comprising white petrolatum (y-axis) versus the percentage of the PEG-400 comprised in the series of compositions (x-axis).
Figure 5:
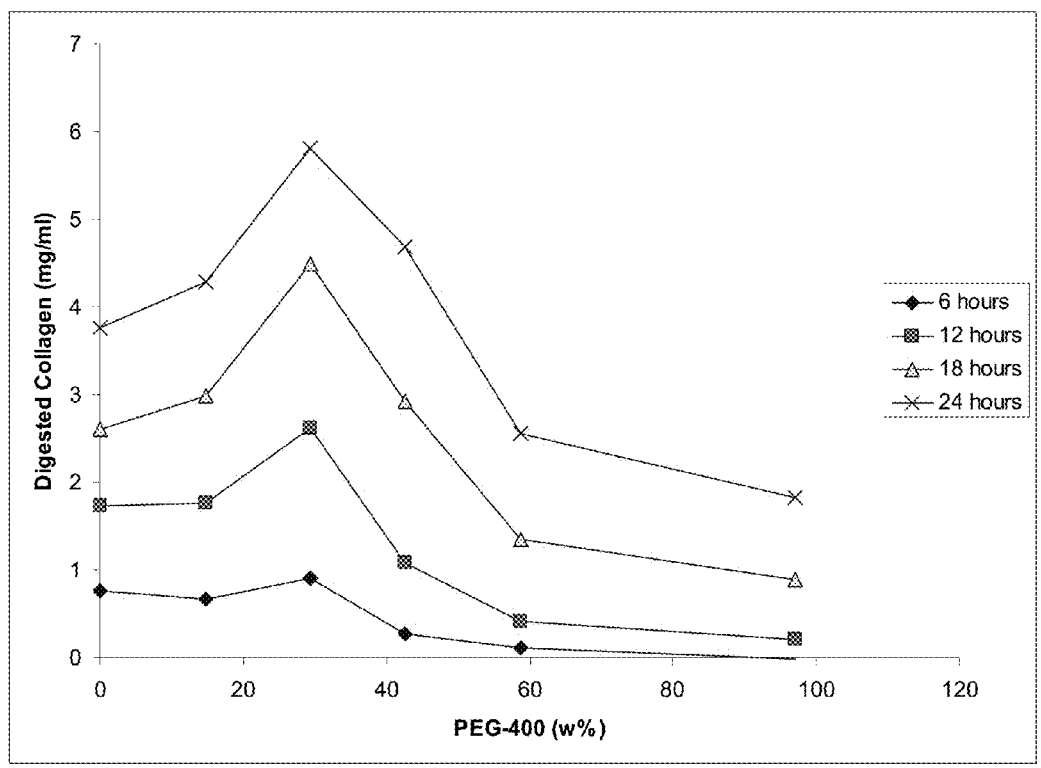
FIG. 5. Plot of the in-vitro collagenolysis activity (mg/ml) of a series of compositions comprising a dispersed phase comprising papain and PEG-400, dispersed in a hydrophobic phase comprising white petrolatum (y-axis) versus the percentage of the PEG-400 comprised in the series of compositions (x-axis).
Figure 6:
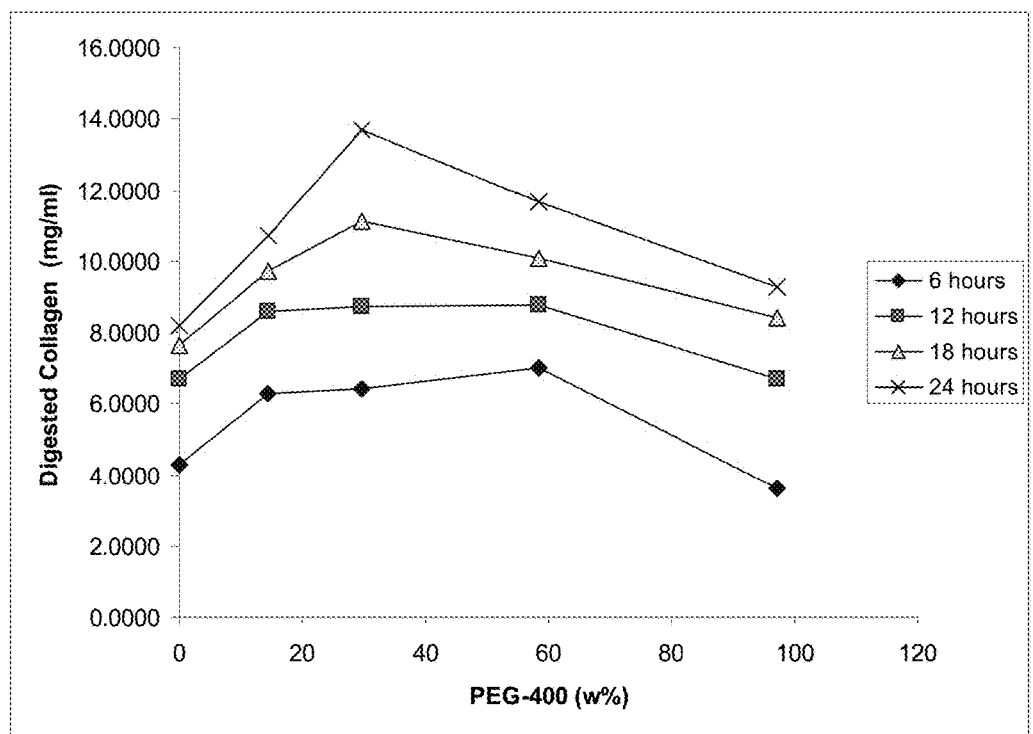
FIG. 6. Plot of the in-vitro collagenolysis activity (mg/ml) of a series of compositions comprising a dispersed phase comprising thermolysin and PEG-400, dispersed in a hydrophobic phase comprising white petrolatum (y-axis) versus the percentage of the PEG-400 comprised in the series of compositions (x-axis).
Figure 7:
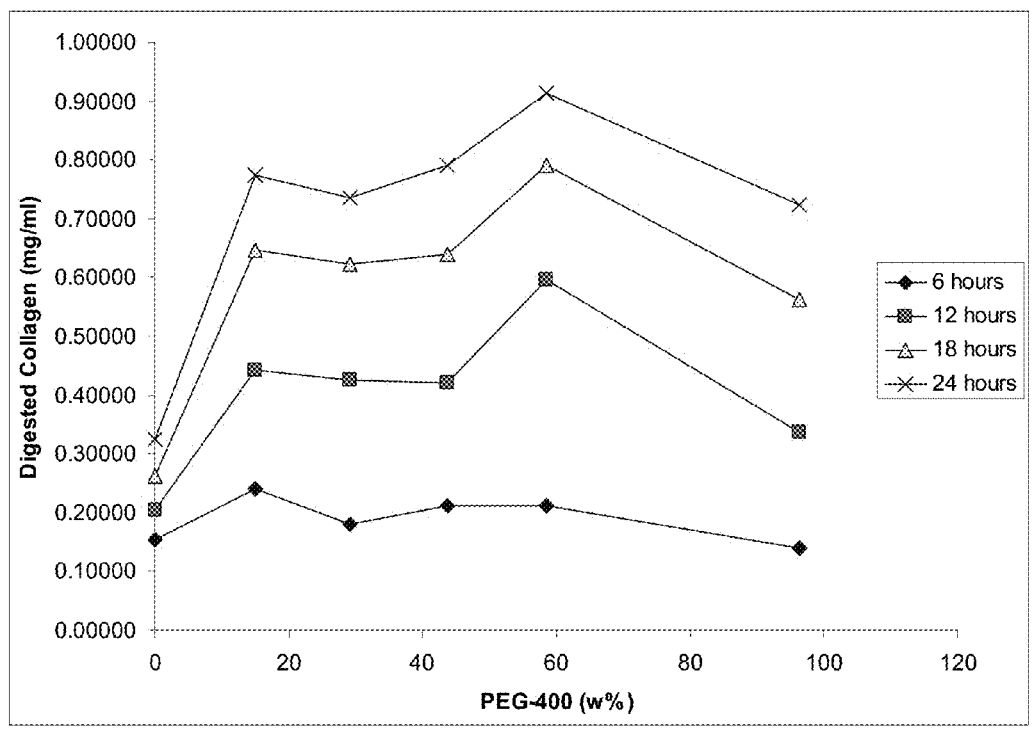
FIG. 7. Plot of the in-vitro collagenolysis activity (mg/ml) of a series of compositions comprising a dispersed phase comprising pepsin and PEG-400, dispersed in a hydrophobic phase comprising white petrolatum (y-axis) versus the percentage of the PEG-400 comprised in the series of compositions (x-axis).
Figure 8:
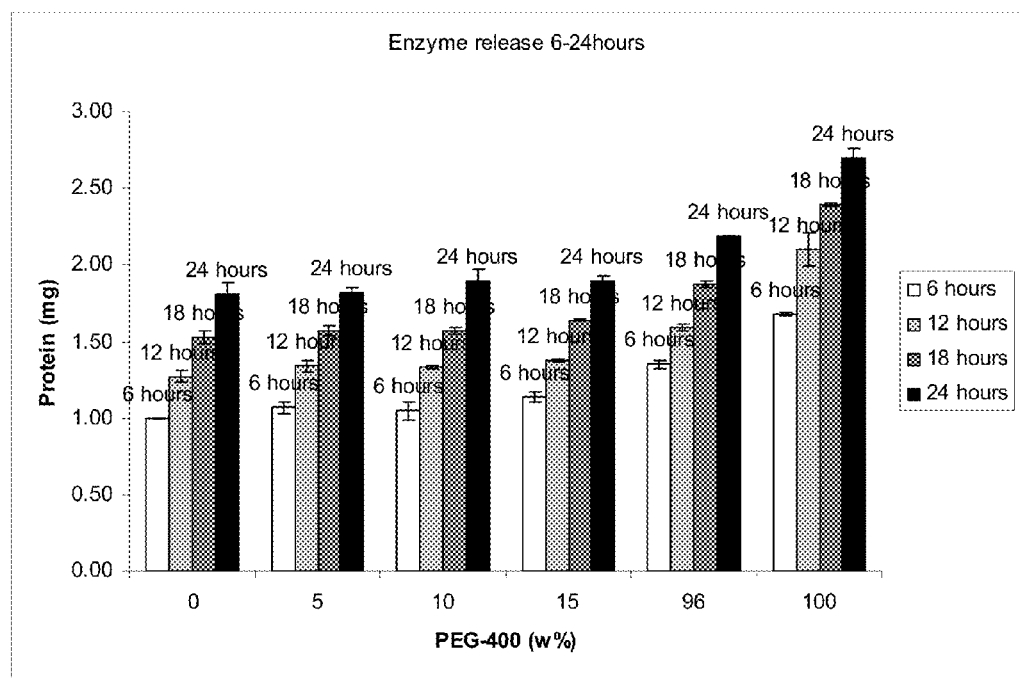
FIG. 8. Plot of the physical release of collagenase (mg) from of a series of compositions comprising a dispersed phase comprising collagenase and PEG-400, dispersed in a hydrophobic phase comprising white petrolatum (y-axis) versus the percentage of the PEG-400 comprised in the series of compositions (x-axis).

It was found, expectedly, that the physical enzyme release in compositions based solely on a hydrophilic vehicle was greater than the release of the enzyme in compositions based solely on a hydrophobic vehicle, and also more than compositions of the present invention. As seen in FIG. 8, the enzyme release profile generally increased with the increasing percentage of hydrophilic polyol (PEG-400), with the highest release at 100% and the lowest release at 0%. However, surprisingly, the enzymatic activity was greater with the dispersion compositions of the present invention (see FIGS. 1-7). Thus the enzymatic activity profile of these dispersion compositions does not correlate with the physical enzyme release profile as would be expected.

The compositions of the present invention are suitable for treatment of a wound in need of debridement by applying to the wound a composition comprising a dispersed phase comprising a hydrophilic polyol, and an effective debriding concentration of at least one proteolytic enzyme; and a continuous phase comprising a hydrophobic base; wherein the amount of hydrophilic polyol is within ±10% w/w of the optimum amount, or ±9%, 8%, 7%, or 6% w/w of the optimum amount, or ±5%, 4%, 3%, 2%, 1%, 0.5%, or 0.1% w/w of the optimum amount of hydrophilic polyol.

These and other non-limiting aspects of the present invention are discussed in further detail in the following sections.

A. Method for Determining the Optimum Amount of Liquid Hydrophilic Polyol

The following protocol can be used to prepare a series of compositions (referred to as "Series of Compositions") and to subsequently determine the optimum amount of liquid hydrophilic polyol that can be used in a dispersion of the present invention:

Eleven (11) compositions can be used to create the Series of Compositions. Note that the amount (% w/w) of proteolytic enzyme in the series of compositions is held constant. The following steps can be used to prepare the eleven (11) compositions:

Determine the ingredients (i.e., liquid hydrophilic polyol, proteolytic enzyme, and hydrophobic base) to be used in the Series of Compositions and select the amount of proteolytic enzyme to be used. By way of example, liquid hydrophilic polyol (e.g., PEG 400), proteolytic enzyme (e.g., collagenase at 1% w/w), and hydrophobic base (e.g., white petrolatum).

(ii) For composition one in the Series of Compositions, use 0% of the liquid hydrophilic polyol, use the selected amount of proteolytic enzyme, and q.s the batch with the hydrophobic base to 100%. For example, and referring to step (i) above, composition one of the Series of Compositions would have: 0% w/w PEG 400, 99% w/w of white petrolatum, and 1% w/w of collagenase.

(iii) For composition two in the Series of Compositions, use 10% w/w of the liquid hydrophilic polyol, the same amount of the proteolytic enzyme, and q.s. the batch with the hydrophobic base to 100%. (Note that it is permissible to use some solid hydrophilic polyol in the makeup of the liquid hydrophilic polyol as necessary to produce a physically stable dispersion for compositions in the Series of Compositions).

(iv) For composition three in the Series of Compositions, use 20% w/w of the liquid hydrophilic polyol, the same amount of the proteolytic enzyme, and q.s. the batch with the hydrophobic base to 100%.

(v) For composition four in the Series of Compositions, use 30% w/w of the liquid hydrophilic polyol, the same amount of the proteolytic enzyme, and q.s. the batch with the hydrophobic base to 100%.

(vi) For composition five in the Series of Compositions, use 40% w/w of the liquid hydrophilic polyol, the same amount of the proteolytic enzyme, and q.s. the batch with the hydrophobic base to 100%.

(vii) For composition six in the Series of Compositions, use 50% w/w of the liquid hydrophilic polyol, the same amount of the proteolytic enzyme, and q.s. the batch with the hydrophobic base to 100%.

(viii) For composition seven in the Series of Compositions, use 60% w/w of the liquid hydrophilic polyol, the same amount of the proteolytic enzyme, and q.s. the batch with the hydrophobic base to 100%.

(ix) For composition eight in the Series of Compositions, use 70% w/w of the liquid hydrophilic polyol, the same amount of the proteolytic enzyme, and q.s. the batch with the hydrophobic base to 100%.

(x) For composition nine in the Series of Compositions, use 80% w/w of the liquid hydrophilic polyol, the same amount of the proteolytic enzyme, and q.s. the batch with the hydrophobic base to 100%.

(xi) For composition ten in the Series of Compositions, use 90% w/w of the liquid hydrophilic polyol, the same amount of the proteolytic enzyme, and q.s. the batch with the hydrophobic base to 100%.

(xii) For composition eleven in the Series of Compositions, use 0% of the hydrophobic base, the same amount of the proteolytic enzyme, and q.s. the batch with the hydrophilic polyol.

(xiii) determine the enzymatic activity of each of the eleven compositions in the Series of Compositions by using the in vitro artificial eschar testing model for the following sample collection times: 6, 12, 18 and 24 hours, as described in Section H of the Detailed Description section of this specification.

(ivx) plot a curve of the enzymatic activity of each composition versus the correlating amount of liquid hydrophilic polyol(s) present in each composition of the Series of Compositions cumulatively for each data collection time. The highest point on the curve for the cumulative 24-hour data collection time correlates to the optimum amount of liquid hydrophilic polyol that can be used in a dispersion.

Further, given that multiple ingredients can be included in the Series of Compositions (e.g., polyol(s) proteolytic enzyme(s), hydrophobic base, and additional ingredients within the dispersed phase, and/or additional ingredients within the continuous hydrophobic phase), the Series of Compositions can be created by (1) varying the amount of hydrophilic polyol as discussed above for each composition in the series, (2) using the determined amount of proteolytic enzyme, and (3) q.s.-ing the batch to 100% with the amount of the additional ingredients including the hydrophobic base; except for composition eleven, where the batch would be q.s.-ed to 100% with the amount of the additional ingredients including the hydrophilic polyol.

B. Method for Determining Whether a Composition has +/−10% w/w of the Optimum Amount of Liquid Hydrophilic Polyol It can be determined if a composition comprising (a) a dispersed phase including a liquid hydrophilic polyol and at least one proteolytic enzyme; and (b) a continuous phase comprising a hydrophobic base (referred to as "Composition of Interest") is within ±10% of the Optimum Amount of liquid hydrophilic polyol by using the following protocol:

Step One: Obtain a Composition of Interest that includes: (i) a dispersed phase including a liquid hydrophilic polyol(s) and a proteolytic enzyme and (ii) a continuous phase including a hydrophobic base.

Step Two: Prepare a series of compositions (referred to as "Series of Compositions") based on the Composition of Interest. Note that the amount (% w/w) of proteolytic enzyme in the Series of Compositions is held constant and is the same as the amount (% w/w) present in the Composition of Interest. The following steps can be used to prepare the Series of Compositions:

Determine the amount of all ingredients in the Composition of Interest (% w/w).

(ii) Determine the total amount of the continuous phase in the Composition of Interest (% w/w). By way of example, if the Composition of Interest includes 15% w/w liquid hydrophilic polyol (e.g., PEG 400), 1% w/w proteolytic enzyme (e.g., collagenase), and 84% w/w hydrophobic base (e.g., white petrolatum), then the Composition of Interest would be 84% w/w continuous phase and 16% w/w dispersed phase.

Step Three: Prepare the Series of Compositions in a manner described above in Section A of this specification (e.g., this would include preparing 11 compositions in a manner described in Section A of this specification).

Step Four: Determine the enzymatic activity of each of the eleven compositions in the Series of Compositions by using the in vitro artificial eschar testing model for each of the following sample collection times: 6, 12, 18 and 24 hours as described in Section H of the Detailed Description section of this specification.

Step Five: Plot a curve of the enzymatic activity of each composition versus the correlating amount of liquid hydrophilic polyol(s) present in each composition of the Series of Compositions cumulatively for each data collection time. The highest point on the curve for the cumulative 24-hour data collection time correlates to the optimum amount of liquid hydrophilic polyol for the Composition of Interest.

Step Six: Compare the amount of liquid hydrophilic polyol present within the Composition of Interest to determine whether it is within ±10% w/w of the optimum amount of liquid hydrophilic polyol for the Composition of Interest.

C. Proteolytic Enzymes

Any proteolytic enzyme useful for wound debridement is suitable for the present invention. Proteolytic enzymes (proteases) break down protein by hydrolysis of the peptide bonds that link amino acids together in the polypeptide chain of a protein. They are divided into four major groups on the basis of catalytic mechanism: serine proteases, cysteine proteases. metalloproteases, and aspartic proteases. Some proteases have been identified with other catalytic amino acids in the active site, such as threonine and glutamic acid; however, they do not form major groups.

1. Serine Proteases

Serine proteases depend upon the hydroxyl group of a serine residue acting as the nucleophile that attacks the peptide bond. The major clans found in humans include the chymotrypsin-like, the subtilisin-like, the alpha/beta hydrolase, and signal peptidase clans. In evolutionary history, serine proteases were originally digestive enzymes. In mammals, they evolved by gene duplication to serve functions in blood clotting, the immune system, and inflammation. These proteases have a broad substrate specificity and work in a wide pH range. Non-limiting examples of serine proteases include trypsin, chymotrypsin, subtilisin, sutilains, plasmin, and elastases.

2. Cysteine Proteases

Peptidases in which the nucleophile that attach the scissile peptide bond in the sulfhydryl group of a cysteine residue are known as cysteine proteases. Cysteine proteases are commonly encountered in fruits including *papaya*, pineapple, and kiwifruit. Cysteine proteases have a broad specificity and are widely used under physiological conditions. In this family, papain has been used extensively for wound debridement for a long time. Other cysteine proteases, such as bromelain and analain, have also been investigated for the applications in wound debridement. Other non-limiting examples of cysteine proteases include calpain, caspases, chymopapain, and clostripain.

3. Metalloproteases

Metalloproteases are among the proteases in which the nucleophilic attach on a peptide bond is mediated by a water molecule, while a divalent metal cation, usually zinc but sometimes cobalt, manganese, nickel or copper, activates the water molecule. The metal ions are extremely important for the activity. Any compounds that have potential to interact with the metal ion, chelating or oxidation, will affect the enzymatic activity. Non-limiting examples of metalloproteases in this family include thermolysin, collagenases, matrix metallo proteinases (MMPs), bacillolysin, dispase, vibriolysin, pseudolysin, stromelysin, and various bacterial derived neutral metalloproteases.

4. Aspartic Peptidases

Aspartic peptidases are so named because aspartic acid residues are the ligands of the activated water molecule. In most enzymes in this family, a pair of aspartic residues act together to bind and activate the catalytic water molecule. All or most aspartic peptidases are endopeptidases. Most aspartic peptidases have a broad specificity. However, the optimum pH of most aspartic peptidases is in the acidic range. Non-limiting examples of aspartic peptidases are pepsin, chymosin, beta-secretase, plasmepsin, plant acid proteases and retroviral proteases.

5. Collagenase

A suitable proteolytic enzyme for wound debridement is the metalloprotease collagenase. The collagenase can be substantially pure or it may contain detectable levels of other proteases.

The potency assay of collagenase, and meaning of "collagenase units" as used herein, is based on the digestion of undenatured collagen from (bovine Achilles tendon) at pH 7.2 and 37° C. for 24 hours. The number of peptide bonds cleaved is measured by reaction with ninhydrin. Amino groups released by a trypsin digestion control are subtracted. One net collagenase unit will solubilize ninhydrin reactive material equivalent to 1 nanomole of leucine equivalents per minute.

The amount (potency or concentration) of collagenase in the compositions of the present invention is at an effective level to debride the wound. Generally, the potency of collagenase in the compositions can vary from about 1 to about 10,000 collagenase units per gram of product, based on the activity of the collagenase used in the product. In various embodiments, the potency, expressed as collagenase units per gram of product, is from about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500 to about 10000, or any range or numerical amount derivable therein.

The concentration of collagenase in the compositions generally can vary from about 0.001% w/w to about 8% w/w. In various embodiments, the concentration, expressed as percentage weight by weight, is from about 0.001, 0.002, 0.003, 0.004, 0.005, 0.006, 0.007, 0.008, 0.009, 0.010 0.015, 0.020, 0.025, 0.030, 0.035, 0.040, 0.050, 0.055, 0.060, 0.065, 0.070, 0.075, 0.080, 0.085, 0.090, 0.095, 0.100, 0.125, 0.150, 0.175, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7 to about 8 or any range or numerical amount derivable therein.

In one embodiment, the collagenase is derived from *Clostridium histolyticum*; however, in other embodiments the collagenase can be derived from other sources. Methods for producing a suitable collagenase are disclosed in U.S. Pat. Nos. 3,705,083; 3,821,364; 5,422,261; 5,332,503; 5,422,103; 5,514,370; 5,851,522; 5,718,897; and 6,146,626 all of which are herein incorporated by reference.

6. Trypsin

Another suitable proteolytic enzyme for wound debridement is the serine protease trypsin. Typically, trypsin is derived from the pancreas of healthy bovine or porcine animals, or both. Trypsin can also be derived from recombinant sources. The pharmaceutical grade (USP/NF) of trypsin is known as Crystallized Trypsin. It contains not less than 2500 USP Trypsin Units per mg, calculated on the dried basis, and not less than 90.0% and not more than 110.0% of the labeled potency. The potency assay of trypsin as well as the definition of a USP Trypsin Unit are found in the Crystallized Trypsin monograph of the USP 31 (Official Aug. 1, 2008) herein incorporated by reference.

The amount (potency or concentration) of trypsin in the compositions of the present invention is at an effective level to debride the wound. Generally, the potency of trypsin in the compositions can vary from about 90 to about 60,000 USP Trypsin Units per gram of product. In various embodiments the potency of trypsin, expressed as USP Trypsin Units per gram of product, is from about 90, 100, 150, 200, 250, 300, 320, 350, 375, 400, 500, 600, 675, 700, 800, 900, 1000, 2000, 3000, 4000, 5000, 10000, 20000, 30000, 40000, 50000 to about 60000, or any range or numerical amount derivable therein.

The concentration of trypsin in the compositions generally can vary from about 0.0025% w/w to about 1% w/w. In various embodiments, the concentration of trypsin, expressed as percent weight by weight, is from about 0.0025, 0.0050, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20 0.25, 0.30, 0.35, 0.40, 0.45, 0.50, 0.55, 0.60, 0.65, 0.70, 0.75, 0.80, 0.85, 0.90, 0.95 to about 1, or any range or numerical amount derivable therein.

D. Hydrophilic Polyols

Hydrophilic polyols of the present invention are water-soluble, polar aliphatic alcohols with at least two hydroxyl groups, and include polymeric polyols, e.g., polyethylene glycols and poloxamers. In one aspect of the invention, the hydrophilic polyol in the dispersed phase is a liquid hydrophilic polyol. In some embodiments, the liquid hydrophilic polyol is a liquid polyethylene glycol or a liquid poloxamer, or mixtures thereof. Solid hydrophilic polyols such as solid polyethylene glycols or solid poloxamers can also be added to the dispersed phase of the invention to help physically stabilize the dispersion. Other examples of liquid hydrophilic polyols include but are not limited to propylene glycol, butylene glycol, pentylene glycol, hexylene glycol, glycerin, hexylene glycol, methoxy polyethylene glycol, propylene carbonate, and ethoxydiglycol, and these may also be added to the dispersed phase.

1. Polyethylene Glycols

Polyethylene glycols are homo-polymers of ethylene glycol and water represented by the formula:

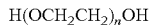

H(OCH$_2$CH$_2$)$_n$OH in which n represents the average number of oxyethylene groups. Polyethylene glycols can be either liquid or solid at 25° C. depending on their molecular weights.

The following suitable non-limiting examples of liquid polyethylene glycols are described using USP nomenclature: polyethylene glycol 200, polyethylene glycol 300, polyethylene glycol 400, polyethylene glycol 500, and polyethylene glycol 600.

The following suitable non-limiting examples of solid polyethylene glycols are described using USP nomenclature: polyethylene glycol 700, polyethylene glycol 800, polyethylene glycol 900, polyethylene glycol 1000, polyethylene glycol 1100, polyethylene glycol 1200, polyethylene glycol 1300, polyethylene glycol 1400, polyethylene glycol 1450, polyethylene glycol 1500, polyethylene glycol 1600, polyethylene glycol 1700, polyethylene glycol 1800, polyethylene glycol 1900, polyethylene glycol 2000, polyethylene glycol 2100, polyethylene glycol 2200, polyethylene glycol 2300, polyethylene glycol 2400, polyethylene glycol 2500, polyethylene glycol 2600, polyethylene glycol 2700, polyethylene glycol 2800, polyethylene glycol 2900, polyethylene glycol 3000, polyethylene glycol 3250, polyethylene glycol 3350, polyethylene glycol 3750, polyethylene glycol 4000, polyethylene glycol 4250, polyethylene glycol 4500, polyethylene glycol 4750, polyethylene glycol 5000, polyethylene glycol 5500, polyethylene glycol 6000, polyethylene glycol 6500, polyethylene glycol 7000, polyethylene glycol 7500, and polyethylene glycol 8000.

The liquid and solid polyethylene glycols are available commercially from the DOW Chemical Company under the CARBOWAX™ tradename and from the BASF Corporation under LUTROL® E and PLURACARE® E tradenames. Both pharmaceutical grade (USP/NF) and cosmetic grade polyethylene glycols are suitable for the present invention.

2. Poloxamers

Poloxamers are synthetic block copolymers of ethylene oxide and propylene oxide represented by the formula:

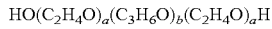

HO(C$_2$H$_4$O)$_a$(C$_3$H$_6$O)$_b$(C$_2$H$_4$O)$_a$H in which formula a and b represent the number of repeat units. Generally a is from 2 to 150 and b is from 15 to 70 depending on the particular poloxamer. Poloxamers can be either liquid or solid at 25° C. depending on their molecular weights.

The following suitable non-limiting examples of liquid poloxamers are described using CTFA/INCI nomenclature: poloxamer 101, poloxamer 105, poloxamer 122, poloxamer 123, poloxamer 124, poloxamer 181, poloxamer 182, poloxamer 183, poloxamer 184, poloxamer 212, poloxamer 231, poloxamer 282, poloxamer 331, poloxamer 401, and poloxamer 402.

The following suitable non-limiting examples of solid poloxamers are described using CTFA/INCI nomenclature: poloxamer 108, poloxamer 188, poloxamer 217, poloxamer 237, poloxamer 238, poloxamer 288, poloxamer 338, poloxamer 407, poloxamer 185, poloxamer 215, poloxamer 234, poloxamer 235, poloxamer 284, poloxamer 333, poloxamer 334, poloxamer 335, and poloxamer 403.

The liquid and solid poloxamers are available commercially from the BASF Corporation under the PLURONIC® and LUTROL® tradenames and from the UNIQEMA Corporation under the SYNPERONIC® trademark. Pharmaceutical grade (USP/NF) poloxamers are poloxamer 124, poloxamer 188, poloxamer 237, poloxamer 338, and poloxamer 407. Both pharmaceutical grade and cosmetic grade poloxamers are suitable for the present invention.

E. Hydrophobic Bases

The hydrophobic bases of the present invention can comprise, but are not limited to, plant, animal, paraffinic, and synthetic derived fats, butters, greases, waxes, solvents, and oils; mineral oils, vegetable oils, petrolatum, water insoluble organic esters and triglycerides, silicones, or fluorinated compounds; or mixtures thereof. In one embodiment of the present invention the hydrophobic phase comprises petrolatum.

Plant derived materials include, but are not limited to, *arachis* (peanut) oil, balsam Peru oil, carnauba wax, candellila wax, castor oil, hydrogenated castor oil, cocoa butter, coconut oil, corn oil, cotton seed oil, jojoba oil, macadamia seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil.

Non-limiting examples of animal derived materials include beeswax, cod liver oil, emu oil, lard, mink oil, shark liver oil, squalane, squalene, and tallow.

Non-limiting examples of paraffinic materials include isoparaffin, microcrystalline wax, heavy mineral oil, light mineral oil, ozokerite, petrolatum, and paraffin.

Suitable non-limiting examples of organic esters and triglycerides include C12-15 alkyl benzoate, isopropyl myristate, isopropyl palmitate, medium chain triglycerides, trilaurin, and trihydroxystearin.

Non-limiting examples of silicones are dimethicone and cyclomethicone. A non-limiting example of a fluorinated compound is polytetrafluoroethylene (PTFE).

1. Petrolatum

Petrolatum is a purified mixture of semisolid hydrocarbons obtained from petroleum and varies from dark amber to light yellow in color. White petrolatum is wholly or nearly decolorized petrolatum and varies from cream to snow white in color. Petrolatum and White Petrolatum can also vary in melting point, viscosity, and consistency.

Various grades are available commercially from the PENRECO Corporation under the tradenames: PENRECO® ULTIMA, PENRECO® SUPER, PENRECO® SNOW, PENRECO® REGENT, PENRECO® LILY, PENRECO® CREAM, PENRECO® ROYAL, PENRECO® BLOND, and PENRECO® AMBER. Various grades are also available commercially from the SONNEBORN Corporation under the tradenames: ALBA®, SUPER WHITE PROTOPET®, SUPER WHITE FONOLINE®, WHITE PROTOPET 1S®, WHITE PROTOPET 2L®, WHITE PROTOPET 3C®, WHITE FONOLINE®, PERFECTA®, YELLOW PROTOPET 2A®, YELLOW FONOLINE®, PROTOLINE®, SONOJELL #4®, SONOJELL #9®, MINERAL JELLY #10®, MINERAL JELLY #14®, MINERAL JELLY #17®, AND CARNATION TROUGH GREASE®.

Petrolatum and White Petrolatum are available in cosmetic grade and pharmaceutical (USP/NF) grade and both are suitable for the present invention.

F. Topical Compositions

The topical compositions of the present invention are dispersions comprising a hydrophilic dispersed phase in a hydrophobic continuous phase. The dispersed phase comprises a proteolytic enzyme and a hydrophilic polyol. In an aspect of the invention, the hydrophilic polyol is a liquid hydrophilic polyol. In some embodiments, the liquid hydrophilic polyol is a liquid polyethylene glycol or a liquid poloxamer, or mixtures thereof. The continuous phase comprises a hydrophobic base. The hydrophobic base can be petrolatum. The compositions are useful for treatment of wounds for wound debridement.

The compositions can be anhydrous as defined herein. The compositions can be semisolid or liquid. The composition can be impregnated on a pad, gauze, or sponge. The compositions can also be sterile.

The compositions can include additional materials known in the art that are suitable for topical compositions of this nature, e.g., absorbents, deodorizers, surfactants, solvents, rheology modifiers, film formers, stabilizers, emollients, moisturizers, preservatives, antimicrobials, antioxidants, chelating agents, fragrances, and colorants.

The compositions can also include additional pharmaceutical active ingredients known in the art that are suitable for topical compositions of this nature, e.g., antimicrobial agents, wound healing agents, anesthetic agents, vulnerary agents, and haemostatic agents. A non-limiting example of a vulnerary agent is balsam Peru.

The compositions can be packaged in any package suitable for dispensing a wound debrider. The compositions can be packaged in multi-use, single-dose, or metered dose packages. Non-limiting examples include a tube, bottle, jar, pump container, pressurized container, bladder container, aerosol container, aerosol spray container, non-aerosol spray container, syringe, pouch, or sachet.

G. Manufacturing Process

The compositions of the present invention can be prepared by techniques and methods known by one of ordinary skill in the art by dissolving or suspending the proteolytic enzyme in part or all of the available hydrophilic polyol. The resulting solution or suspension can be mixed with a hydrophobic base to form a dispersion, wherein the hydrophobic base becomes the continuous phase and the hydrophilic polyol/enzyme phase becomes the dispersed phase. These compositions can be prepared using processing equipment known by one of ordinary skill in the art, e.g., blenders, mixers, mills, homogenizers, dispersers, dissolvers, etc.

H. In Vitro Artificial Eschar Testing Model

Enhancement of the enzymatic activity of the compositions was established by testing the compositions using an in vitro artificial eschar model as described below and in the publication "*Study on the debridement efficacy of formulated enzymatic wound debriding agents by in vitro assessment using artificial wound eschar and by an in vivo pig model*", Shi et. al., *Wound Repair Regen*, 2009, 17(6):853, herein incorporated by reference. Bovine collagen (Type I), bovine fibrinogen, and elastin were used to make an Artificial Wound Eschar (AWE) substrate. Collagen-FITC labeled, elastin-rhodamine, and fibrin-coumarin were the raw materials used for producing the AWE substrate. To prepare 1 gram of AWE substrate, 650 mg Collagen-FITC and 100 mg each of elastin-rhodamine and fibrin-coumarin were weighed into a 50 mL tube and homogenized in 10 mL of Tris buffer saline. In a separate tube, 10 mL of fibrinogen solution was prepared at 15 mg/mL with Tris buffer saline. The two solutions were combined and thoroughly mixed. A thrombin solution (0.25 mL at 50 U/mL) was added, quickly mixed, and the solution was poured into a Petri dish containing a 90 mm nonreactive membrane filter. As a result of the thrombin-induced fibrinogen polymerization, the material began to form a soft sheet on top of the membrane filter by clotting the dyed proteins into a solid matrix. The clotted AWE substrate was allowed to solidify for 30 minutes and then rinsed with water for 15 minutes to remove the thrombin. The AWE substrate was further dehydrated to 75% moisture content in preparation for use.

With the AWE substrate still attached to the membrane, a 35 mm diameter piece was punched out using a hole punch. The AWE substrate punch was placed on the top flat face of a Franz Diffusion Cell System (Hanson Research, Chatsworth, Calif.), and a TEFLON® sample holder placed on top. The debriding ointment samples were loaded in the center of the sample holder, and any excess sample was removed by scraping. The solution in the receptor cells was Tris buffer at a pH of 7.4 for samples containing collagenase, papain, thermolysin, or trypsin; and was sodium acetate buffer at a pH of 2 for samples containing pepsin. The solution in receptor cells was sampled in 1 mL increments at the following sample collection times: 0, 1, 2, 3, 6, 12, 18 and 24 hours. Once finished, the samples were analyzed by fluorescence measurement of FITC dye at 485 nm (excitation wavelength) and 520 nm (emission wavelength) to determine the digestion of collagen (collagenolysis) reported in mg/ml.

In-Vitro Physical Enzyme Release Test

The release of enzyme from the compositions was determined by a Franz cell diffusion study using PVDF (0.45 micron) filters. This study was performed at 35° C. and lasted for 6 hours. The solution samples in the receptor cells were subjected to a total protein analysis.

The protein concentration was determined by a BCA assay (Peirce) while the same collagenase was used as the reference standard. The details are described as follows.

The BCA Protein Assay combines the well-known reduction of $Cu^{2+}$ to $Cu^{1+}$ by protein in an alkaline medium with the highly sensitive and selective colorimetric detection of the cuprous cation ($Cu^{1+}$) by bicinchoninic acid. The first step is the chelation of copper with protein in an alkaline environment to form a blue-colored complex. In this reaction, known as the biuret reaction, peptides containing three or more amino acid residues form a colored chelate complex with cupric ions in an alkaline environment containing sodium potassium tartrate. This became known as the biuret reaction because a similar complex forms with the organic compound biuret ($NH_2$—CO—NH—CO—$NH_2$) and the cupric ion. Biuret, a product of excess urea and heat, reacts with copper to form a light blue tetradentate complex. In the second step of the color development reaction, BCA, a highly sensitive and selective colorimetric detection reagent reacts with the cuprous cation ($Cu^{1+}$) that was formed in step 1. The purple-colored reaction product is formed by the chelation of two molecules of BCA with one cuprous ion. The BCA/copper complex is water-soluble and exhibits a strong linear absorbance at 562 nm with increasing protein concentrations. The purple color may be measured at any wavelength between 550 nm and 570 nm with minimal (less than 10%) loss of signal. See the following reference herein incorporated by reference: Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D. C. (1985). Measurement of protein using bicinchoninic acid. Anal. Biochem. 150, 76-85.

EXAMPLES

The following examples are included to demonstrate certain non-limiting aspects of the invention. It should be appreciated by those of skill in the art that the techniques disclosed in the examples which follow represent techniques discovered by the applicants to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1: Dispersions of Collagenase/PEG 400 in Petrolatum

The dispersions in TABLE 1 were prepared with varying concentrations of Polyethylene Glycol 400 (PEG-400) dispersed in Petrolatum.

TABLE 1

| Dispersion | PEG 400 % w/w | PEG-1450 % w/w | Wht Petrolatum % w/w | Poloxamer 407 % w/w | Collagenase % w/w |
|---|---|---|---|---|---|
| A | 0 | 0 | 99.8 | 0 | 0.2 |
| B | 10 | 0 | 89.8 | 0 | 0.2 |
| C | 15 | 0 | 84.8 | 0 | 0.2 |
| D | 20 | 0 | 79.9 | 0.4 | 0.2 |
| E | 30 | 0 | 69 | 0.9 | 0.2 |
| F | 50 | 0 | 49.3 | 1.2 | 0.2 |
| G | 68 | 0 | 29.8 | 2.0 | 0.2 |
| H* | 83 | 12.5 | 4.5 | 0 | 0.2 |
| I* | 70 | 29.8 | 0 | 0 | 0.2 |

*PEG-1450 was added to PEG-400 to form a semi-solid resulting in approximate total PEG of 96% and 100% respectively.

The enzymatic debridement activity of each dispersion was determined by the in-vitro artificial eschar model described above and the results plotted in FIG. 1. As can be seen by the results in FIG. 1, the optimum amount of PEG-400 based on the 24 hour curve is about 20% w/w PEG-400.

Example 2: Dispersions of Collagenase/PEG 600 in Petrolatum

The dispersions in TABLE 2 were prepared with varying concentrations of Polyethylene Glycol 600 (PEG-600) dispersed in Petrolatum.

TABLE 2

| Dispersion | PEG 600 % w/w | Wht Petrolatum % w/w | Poloxamer 407 % w/w | Collagenase % w/w |
|---|---|---|---|---|
| J | 0 | 99.8 | 0 | 0.2 |
| K | 10 | 89.525 | 0.275 | 0.2 |
| L | 20 | 79.248 | 0.552 | 0.2 |
| M | 30 | 68.973 | 0.827 | 0.2 |
| N | 50 | 48.42 | 1.38 | 0.2 |
| O | 80 | 17.59 | 2.21 | 0.2 |
| P | 97 | 0 | 2.8 | 0.2 |

The enzymatic debridement activity of each dispersion was determined by the in-vitro artificial eschar model described above. The results are plotted in FIG. 2. As can be seen by the results in FIG. 2, the optimum amount of PEG-600 based on the 24 hour curve is about 30% w/w PEG-600.

Example 3: Dispersions of Collagenase/Poloxamer 124 in Petrolatum

The dispersions in TABLE 3 were prepared with varying concentrations of Poloxamer 124 dispersed in Petrolatum.

TABLE 3

| Dispersion | Poloxamer 124 % w/w | Wht Petrolatum % w/w | Poloxamer 407 % w/w | Collagenase % w/w |
|---|---|---|---|---|
| Q | 0 | 99.8 | 0 | 0.2 |
| R | 10 | 89.8 | 0 | 0.2 |
| S | 20 | 79.8 | 0 | 0.2 |
| T | 30 | 69.8 | 0 | 0.2 |
| U | 50 | 48.14 | 1.66 | 0.2 |
| V | 80 | 17.14 | 2.66 | 0.2 |
| W | 85* | 0 | 15 | 0.2 |

*Poloxamer 407 was added to Poloxamer 124 to form a semi-solid resulting in approximate total of Poloxamer of 100%

The enzymatic debridement activity of each dispersion was determined by the in-vitro artificial eschar model described above. The results are plotted in FIG. 3. As can be seen by the results in FIG. 3, the optimum amount of Poloxamer 124 based on the 24 hour curve is about 30% w/w Poloxamer 124.

Example 4: Dispersions of Trypsin/PEG 400 in Petrolatum

The dispersions in TABLE 4 were prepared with varying concentrations of Polyethylene Glycol 400 (PEG-400) dispersed in Petrolatum.

TABLE 4

| Dispersion | PEG 400 % w/w | PEG 1450 % w/w | Wht Petrolatum % w/w | Poloxamer 407 % w/w | Trypsin % w/w |
|---|---|---|---|---|---|
| X | 0 | 0 | 99.8 | 0 | 0.2 |
| Y | 14 | 0 | 84.9 | 0.4 | 0.2 |
| Z | 29 | 0 | 69.8 | 0.9 | 0.2 |
| AA | 59 | 0 | 39.16 | 1.64 | 0.2 |
| BB | 80 | 0 | 17.06 | 2.74 | 0.2 |
| CC | 82* | 15.2 | 0 | 2.6 | 0.2 |

*PEG-1450 was added to PEG-400 to form a semi-solid resulting in approximate total PEG of 97%

The enzymatic debridement activity of each dispersion was determined by the in-vitro artificial eschar model described above. The results are plotted in FIG. 4. As can be seen by the results in FIG. 4, the optimum amount of PEG-400 based on the 24 hour curve is about 14% w/w PEG-400.

Example 5: Dispersions of Papain/PEG 400 in Petrolatum

The dispersions in TABLE 5 were prepared with varying concentrations of Polyethylene Glycol 400 (PEG-400) dispersed in Petrolatum.

TABLE 5

| Dispersion | PEG 400 % w/w | PEG 1450 % w/w | Wht Petrolatum % w/w | Poloxamer 407 % w/w | Papain % w/w |
|---|---|---|---|---|---|
| DD | 0 | 0 | 99.85 | 0 | 0.15 |
| EE | 15 | 0 | 85.05 | 0.4 | 0.15 |
| FF | 29 | 0 | 69.82 | 0.83 | 0.15 |
| GG | 43 | 0 | 54.85 | 1.24 | 0.15 |
| HH | 59 | 0 | 39.694 | 1.636 | 0.15 |
| II | 82* | 15.01 | 0 | 2.67 | 0.15 |

*PEG-1450 was added to PEG-400 to form a semi-solid resulting in approximate total PEG of 97%

The enzymatic debridement activity of each dispersion was determined by the in-vitro artificial eschar model described above. The results are plotted in FIG. 5. As can be seen by the results in FIG. 5, the optimum amount of PEG-400 based on the 24 hour curve is about 29% w/w PEG-400.

Example 6: Dispersions of Thermolysin/PEG 400 in Petrolatum

The dispersions in TABLE 6 were prepared with varying concentrations of Polyethylene Glycol 400 (PEG-400) dispersed in Petrolatum.

TABLE 6

| Dispersion | PEG 400 % w/w | PEG 1450 % w/w | Wht Petrolatum % w/w | Poloxamer 407 % w/w | Thermolysin % w/w |
|---|---|---|---|---|---|
| JJ | 0 | 0 | 99.85 | 0 | 0.15 |
| KK | 14 | 0 | 85.05 | 0.4 | 0.15 |
| LL | 29 | 0 | 69.82 | 0.83 | 0.15 |
| MM | 59 | 0 | 39.694 | 1.636 | 0.15 |
| NN | 82* | 15.01 | 0 | 2.67 | 0.15 |

*PEG-1450 was added to PEG-400 to form a semi-solid resulting in approximate total PEG of 97%

The enzymatic debridement activity of each dispersion was determined by the in-vitro artificial eschar model described above. The results are plotted in FIG. 6. As can be seen by the results in FIG. 6, the optimum amount of PEG-400 based on the 24 hour curve is about 29% w/w PEG-400.

Example 7: Dispersions of Pepsin/PEG 400 in Petrolatum

The dispersions in TABLE 7 were prepared with varying concentrations of Polyethylene Glycol 400 (PEG-400) dispersed in Petrolatum.

TABLE 7

| Dispersion | PEG 400 % w/w | PEG 1450 % w/w | Wht Petrolatum % w/w | Poloxamer 407 % w/w | Pepsin % w/w |
|---|---|---|---|---|---|
| OO | 0 | 0 | 99 | 0 | 1 |
| PP | 15 | 0 | 84.2 | 0.4 | 1 |
| QQ | 29 | 0 | 68.97 | 0.83 | 1 |
| RR | 44 | 0 | 54.005 | 1.24 | 1 |
| SS | 58 | 0 | 38.844 | 1.636 | 1 |
| TT | 81* | 15.01 | 0 | 2.67 | 1 |

*PEG-1450 was added to PEG-400 to form a semi-solid resulting in approximate total PEG of 96%

The enzymatic debridement activity of each dispersion was determined by the in-vitro artificial eschar model described above. The results are plotted in FIG. 7. As can be seen by the results in FIG. 7, the optimum amount of PEG-400 based on the 24 hour curve is about 58% w/w PEG-400.

Example 8: Dispersions of Collagenase/PEG 400 in Petrolatum for Physical Release of Enzyme The dispersions in TABLE 8 were prepared with varying concentrations of Polyethylene Glycol 400 (PEG-400) dispersed in Petrolatum.

TABLE 8

| Dispersion | PEG 400 % w/w | PEG 1450 % w/w | Wht Petrolatum % w/w | Collagenase % w/w |
|---|---|---|---|---|
| UU | 0 | 0 | 99.8 | 0.2 |
| VV | 5 | 0 | 94.8 | 0.2 |
| WW | 10 | 0 | 89.8 | 0.2 |
| XX | 15 | 0 | 84.8 | 0.2 |
| YY | 83* | 12.5 | 4.5 | 0.2 |
| ZZ | 70* | 29.8 | 0 | 0.2 |

*PEG-1450 was added to PEG-400 to form a semi-solid resulting in approximate total PEG of 83% and 100% respectively.

The physical release of enzyme was determined by the In-vitro Physical Enzyme Release Test as described above. The results are plotted in FIG. 8. As can be seen by the results in FIG. 8, the physical release of collagenase generally increased as the concentration of PEG-400 in the dispersion increased with the highest release at 100% and the lowest release at 0% PEG-400.

As can be seen by the results shown herein, the physical enzyme release profile of the dispersions as a function of increased concentration of hydrophilic polyol does not correlate to the enzymatic activity profile of the enzyme as a function of increased concentration of hydrophilic polyol.

Example 9: Stability and Efficacy Data

Figure 9:
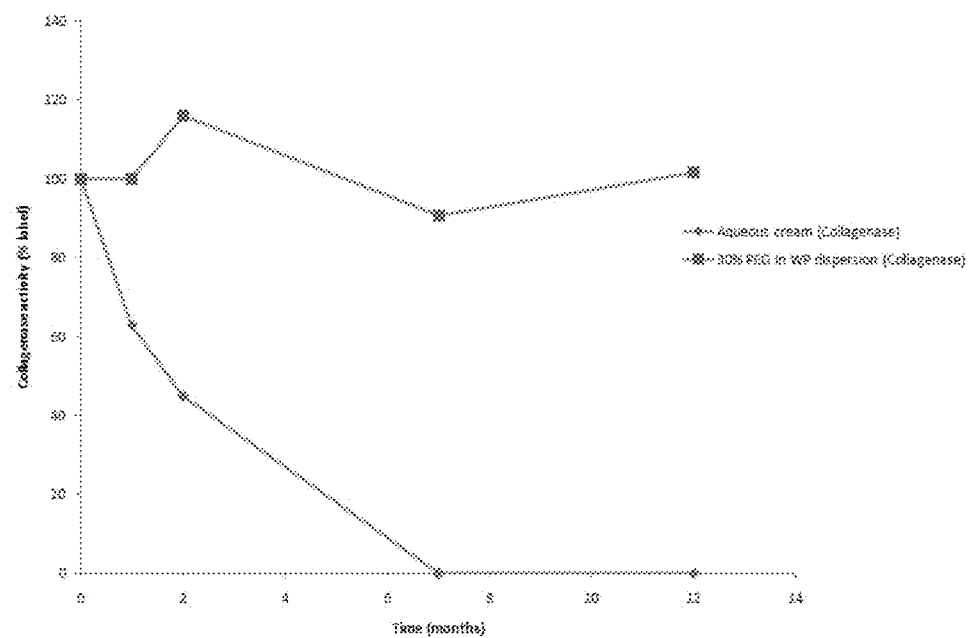
FIG. 9. Enzyme stability in PEG-in-white petrolatum dispersion compared with oil-in-water emulsion cream.

FIG. 9 provides data comparing the stability of collagenase in a dispersion of the present invention ("30% PEG in WP dispersion") and an oil-in-water emulsion ("Aqueous cream"). These data suggest that collagenase was more stable in the 30% PEG in WP dispersion when compared to the Aqueous cream. Tables 9-10 provide descriptions of the 30% PEG in WP dispersion and Aqueous cream formulations.

TABLE 9

(30% PEG in WP dispersion)*

| Ingredients | wt % |
|---|---|
| PEG-600 | 30.059774 |
| Poloxamer-407 | 1.5078044 |
| White Petrolatum | 68.309516 |
| Collagenase | 0.1228163 |
| TOTAL | 100 |

*PEG in WP dispersion was prepared as follows: (A) Active Phase: (1) 9.71 grams of PEG-600 and 0.2361 grams of collagenase were mixed for 20 minutes at room temperature (20-25° C.) for 45 min. (B) Main Phase: (1) 102.784 grams of white petrolatum, 37.65 grams of PEG-600, and 2.27 grams of poloxamer-407 were mixed at 70° C. until uniform; (2) the mixture was cooled to 40-45° C. Added 7.79 grams of the Active Phase was added to the Main Phase followed by stirring for 30 minutes or until homogenous mixture obtained.

TABLE 10

(Aqueous cream)*

| Ingredients | wt % |
|---|---|
| Isopropyl Myristate | 30.57437 |
| Emulsifying Wax | 4.502116 |
| White Petrolatum | 20.369574 |
| Incroquat TMS | 4.502116 |
| Water | 20.009404 |
| Glycerin (96%) | 19.839324 |
| Collagenase | 0.2030955 |
| TOTAL | 100 |

*Aqueous cream was prepared as follows: (A) Active Phase: (1) 0.2 grams of collagenase was mixed with 20 grams of deionized water. (B) Main Phase: (1) 20.36 grams of white petrolatum was mixed with 4.5 grams of emulsifying wax, 4.5 grams of Incroquate TMS, and 19.83 grams of glycerin (96%) at 70° C. until uniform; (2) the mixture was cooled to 35-40° C. Added Active Phase to Main Phase followed by stirring for 30 minutes or until homogenous mixture obtained.

Figure 10:
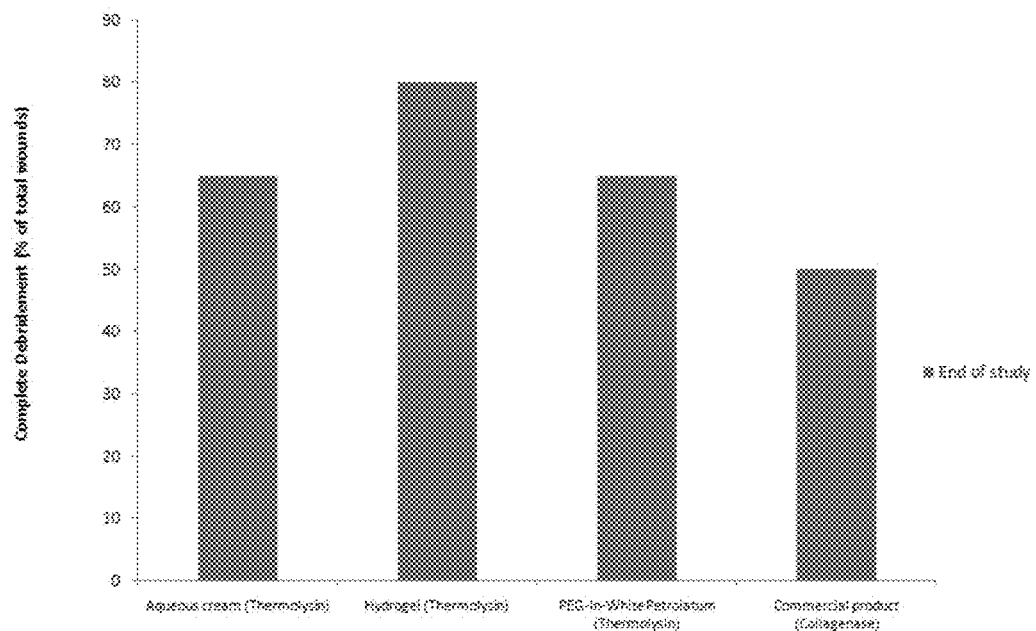
FIG. 10. Debridement efficacy in Eschar removal in pig burn wound.

FIG. 10 provides data comparing enzyme debridement efficacy in eschar removal in pig burn wounds of a dispersion of the present invention ("PEG-in-White Petrolatum"—Table 11) to the following three formulations: (1) an Aqueous cream—Table 12; (2) SANTYL® ("Commercial product", which is a mixture of collagenase and white petrolatum); and a hydrogel formulation—Table 13. The burn wounds were created on pigs and hard eschars formed after several days. Formulation was applied to the hard eschars one a day for two weeks. Only fully debrided wounds were counted as "complete debridement." There were a total of 20 wounds per treatment.

TABLE 11

(PEG-in-White Petrolatum)*

| Ingredients | wt % |
|---|---|
| Poloxamer-407 | 0.99891551 |
| White Petrolatum | 78.7544989 |
| Thermolysin | 0.20168104 |
| PEG-600 | 20.0449046 |
| TOTAL | 100 |

*PEG-in-White Petrolatum was prepared as follows: (A) Active Phase: (1) 32.67 grams of PEG-600 and 1.63 grams of Poloxamer-407 were homogenized at 70° C. until mixture was clear; (2) mixture was cooled to about 35° C.; and (3) thermolysin was and mixed for at least 30 min.. (B) Main Phase: (1) 236.52 grams of white petrolatum, 30.05 grams of PEG-600, and 1.5 grams of poloxamer-407 were homogenized at 70° C.; and (2) mixture was cooled to about 35° C. The Active Phase (B) was added to the Main Phase (B) and mixed at room temperature (20-25° C.) for 45 min.

TABLE 12

(Aqueous Cream)*

| Ingredients | wt % |
|---|---|
| Emulsifying Wax | 14.993927 |
| 1% KH2PO4 in water (pH = 7.5) | 74.057507 |
| Isopropyl Palmitate, NF | 5.4571649 |
| Glycerin | 5.0104708 |
| Thermolysin | 0.2001065 |
| Methyl paraben | 0.2007937 |
| Propyl paraben | 0.0800301 |
| TOTAL | 100 |

*Aqueous cream was prepared as follows: (1) parabens were melted in buffer at high temperature (>70° C.) along with glycerin; (2) emulsifying wax and isopropyl palmitate were added; (3) the mixture was mixed at high temperature for 45 min and then cooled to about 35° C.; (4) thermolysin was added as a slurry in the buffer; (5) the mixture was cooled to room temperature (20-25° C.).

TABLE 13

| (Hydrogel)* | |
|---|---|
| Ingredients | wt % |
| Hydroxypropylmethylcellulose | 2.250621745 |
| 1% KH2PO4 in water (pH = 7.5) | 77.96851753 |
| Thermolysin | 0.202530294 |
| Methyl paraben | 0.244719829 |
| Propyl paraben | 0.0480663 |
| Propylene glycol | 19.28554438 |
| TOTAL | 100 |

*Hydrogel was prepared as follows: (1) parabens and propylene glycol were solubilized in water at 70° C.; (2) HPMC was added at room temperature (20-25° C.); (3) Thermolysin was added and a milky viscous solution formed.

The invention claimed is:

1. An enzymatic wound debriding composition comprising:
   (a) a hydrophobic dispersed phase comprising an amount of PEG 400 providing the maximum enzymatic activity of the composition, and thermolysin; and
   (b) a hydrophobic continuous phase comprising a hydrophobic base, wherein the hydrophilic dispersed phase is dispersed in the hydrophobic continuous phase,
   wherein the amount of PEG 400 is from 19-39% w/w of the composition,
   wherein the composition is anhydrous, and
   wherein said hydrophobic base is selected from the group consisting of isoparaffin, microcrystalline wax, heavy mineral oil, light mineral oil, ozokerite, petrolatum, paraffin, and combinations thereof.

2. The enzymatic wound debriding composition of claim 1, wherein the hydrophobic base is petrolatum.

3. The enzymatic wound debriding composition of claim 1, wherein the amount of PEG 400 is from 22-36% w/w of the composition.

4. The enzymatic wound debriding composition of claim 1, wherein the amount of PEG 400 is 29% w/w of the composition.

5. The enzymatic wound debriding composition of claim 1, wherein the composition is a liquid.

6. The enzymatic wound debriding composition of claim 1, wherein the composition is a semi-solid.

7. The enzymatic wound debriding composition of claim 1, wherein the composition is sterile.

8. A method of debriding a wound in need of debridement, the method comprising applying to the wound an effective amount of an anhydrous enzymatic composition to debride the wound, the anhydrous enzymatic composition comprising:
   a) a hydrophobic dispersed phase comprising an amount of PEG 400 providing the maximum enzymatic activity of the composition, and thermolysin; and
   (b) a hydrophobic continuous phase comprising a hydrophobic base, wherein the hydrophilic dispersed phase is dispersed in the hydrophobic continuous phase,
   wherein the amount of PEG 400 is from 19-39% w/w of the composition, and
   wherein said hydrophobic base is selected from the group consisting of isoparaffin, microcrystalline wax, heavy mineral oil, light mineral oil, ozokerite, petrolatum, paraffin, and combinations thereof.

9. The method of claim 8, wherein the hydrophobic base is petrolatum.

10. The method of claim 8, wherein the amount of PEG 400 is from 22-36% w/w of the composition.

11. The method of claim 8, wherein the amount of PEG 400 is 29% w/w of the composition.

12. The method of claim 8, wherein the composition is a liquid.

13. The method of claim 8, wherein the composition is a semi-solid.

14. The method of claim 8, wherein the composition is sterile.

* * * * *